(12) United States Patent
Knappe et al.

(10) Patent No.: US 9,999,584 B2
(45) Date of Patent: *Jun. 19, 2018

(54) AGENT AND METHOD FOR TEMPORARILY DEFORMING KERATIN-CONTAINING FIBERS

(71) Applicant: Henkel AG & Co. KGaA, Duesseldorf (DE)

(72) Inventors: Thorsten Knappe, Schenefeld (DE); Pamela Kaftan, Hamburg (DE); Maria Catalina Bermudez Agudelo, Hamburg (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/363,393

(22) Filed: Nov. 29, 2016

(65) Prior Publication Data

US 2017/0165172 A1 Jun. 15, 2017

(30) Foreign Application Priority Data

Dec. 15, 2015 (DE) .......................... 10 2015 225 205

(51) Int. Cl.
| | |
|---|---|
| *A61K 8/81* | (2006.01) |
| *A61K 8/04* | (2006.01) |
| *A61K 8/31* | (2006.01) |
| *A61K 8/33* | (2006.01) |
| *A61K 8/34* | (2006.01) |
| *A61Q 5/06* | (2006.01) |
| *B65D 83/14* | (2006.01) |

(52) U.S. Cl.
CPC ............ *A61K 8/8152* (2013.01); *A61K 8/046* (2013.01); *A61K 8/31* (2013.01); *A61K 8/315* (2013.01); *A61K 8/33* (2013.01); *A61K 8/34* (2013.01); *A61K 8/8147* (2013.01); *A61Q 5/06* (2013.01); *A61K 2800/594* (2013.01); *A61K 2800/87* (2013.01); *B65D 83/752* (2013.01)

(58) Field of Classification Search
CPC ...... A61K 8/31; A61K 8/8147; A61K 8/8152; A61Q 5/06

See application file for complete search history.

(56) References Cited

U.S. PATENT DOCUMENTS

| | | | |
|---|---|---|---|
| 4,874,604 A | 10/1989 | Sramek | |
| 5,176,898 A | 1/1993 | Goldberg et al. | |
| 2008/0178899 A1* | 7/2008 | Moenks | ................. A61K 8/046 |
| | | | 132/203 |
| 2014/0093469 A1 | 4/2014 | Mueller et al. | |

FOREIGN PATENT DOCUMENTS

| | | |
|---|---|---|
| EP | 1719499 A1 | 11/2006 |
| EP | 1719500 A1 | 11/2006 |
| EP | 1726331 A1 | 11/2006 |
| WO | 2005012588 A1 | 2/2005 |
| WO | 2012054278 A2 | 4/2012 |

OTHER PUBLICATIONS

ACUDYNE™ Hair Styling Polymers Product Overview (DOW May 2015; 4 pages) (Year: 2015).*
Preliminary Amendment for U.S. Appl. No. 15/360,270, dated Nov. 23, 2016.
U.S. Appl. No. 15/360,270, dated Nov. 23, 2016.
Intellectual Property Office, Combined Search and Examination Report under Sections 17 and 18(3) for United Kingdom Application No. GB1621141.9 dated Sep. 29, 2017.
Institute National De La Propriete Industrielle, Preliminary Search Report for French Application No. 1662101 dated Oct. 31, 2017.
The Dow Chemical Company, "ACUDYNE Hair Styling Polymers Product Overview," May 2015, pp. 1-4, retrieved from the internet on Jan. 31, 2018 at: http://msdssearch.dow.com/PublishedLiteratureDOWCOM/dh_0933/0901b80380933ea9.pdf?filepath=personalcare/pdfs/noreg/324-00624.pdf&fromPage=GetDoc.

* cited by examiner

*Primary Examiner* — Ernest V Arnold
(74) *Attorney, Agent, or Firm* — Lorenz & Kopf LLP

(57) ABSTRACT

Cosmetic agents for temporarily deforming keratinic fibers and methods for temporarily deforming keratinic fibers using the cosmetic agents are provided. In an embodiment, a cosmetic agent comprises:
   a) a cosmetic preparation comprising:
      a1) at least one copolymer comprising at least the following monomer units:
         (meth)acrylic acid;
         (meth)acrylic acid alkyl ester; and
         (meth)acrylic acid hydroxy alkyl ester; and
      a2) at least one copolymer comprising at least the following monomer units:
         styrene; and
         acrylic acid and/or methacrylic acid,
   wherein the proportion by weight of copolymers a1) and a2) in the total weight of the cosmetic preparation is about 10 to about 30% by weight.

19 Claims, No Drawings

AGENT AND METHOD FOR TEMPORARILY DEFORMING KERATIN-CONTAINING FIBERS

CROSS-REFERENCE TO RELATED APPLICATION

This application claims priority to German Patent Application No. 10 2015 225 205.1, filed Dec. 15, 2015, which is incorporated herein by reference in its entirety.

TECHNICAL FIELD

The present disclosure relates to a cosmetic composition for hair setting or for temporarily reshaping keratinic fibers, in particular human hair, wherein the composition contains a combination of two specific copolymers in high concentration.

BACKGROUND

The temporary creation of hairstyles for a longer period of time lasting up to a number of days generally requires the use of firming active substances. Hair treatment agents that serve to temporarily shape the hair thus play an important role. Appropriate agents for temporary deformation usually contain synthetic polymers and/or waxes as firming active substance. Agents for assisting the temporary reshaping of keratin-containing fibers can be produced, by way of example, in the form of hairspray, hair wax, hair gel or hair mousse.

The most important property of an agent for temporarily deforming hair, also referred to hereinafter as a styling agent, lies in being able to provide the treated fibers with the greatest possible hold in the newly modeled form—i.e. a form impressed on the hair. Reference is also made to a strong hairstyle hold or to a high holding power of the styling agent. The hold of a hairstyle is determined fundamentally by the type and quantity of the used firming active substances, however the further constituents of the styling agent can also have an effect.

Besides a high holding power, styling agents must also satisfy a wide range of further requirements. These can be divided roughly into properties on the hair, properties of the respective formulation, for example properties of sprayed aerosols, and properties that concern the handling of the styling agent, wherein the properties on the hair are attributed particular importance. In particular, moisture resistance, low stickiness (tack), and a balanced conditioning effect can be cited. Furthermore, a styling agent should be universally usable for all hair types where possible and should be mild on the hair and skin.

In order to satisfy the different requirements, a multiplicity of synthetic polymers which are used in styling agents have been developed as firming active substances. These polymers can be divided into cationic, anionic, non-ionic and amphoteric firming polymers.

European patents EP 1719499 B1, EP 1719500 B1 and EP 1726331 B1 describe acrylate resins with the INCI name Acrylates/Hydroxy Ester Acrylates Copolymer and use thereof in styling agents. International patent application WO 2012/054278 A2 also mentions Acrylates/Hydroxy Ester Acrylates Copolymers as hair-firming polymers and, as an example, uses Acudyne® 1000 (The Dow Chemical Company) in hair mousses.

Hair-firming agents based on copolymers of styrene with (meth)acrylic acid and/or esters thereof are described in international patent application WO2012/168035 A1.

Not any polymer or not any polymer blend is suitable in principle for the production of hair-styling agents. This is true in particular for hairsprays, in which case the viscosity for example and thus also the spray behavior is influenced by the polymer or the quantity of the used polymer.

Furthermore, not any polymer and any polymer mixture are suitable for producing highly concentrated hair-styling agents. Besides the previously described problems with the viscosity and dosing of the agents, difficulties also occur with regard to the solubility and the storage stability, in particular of hairsprays, with rising polymer concentration.

A hairspray with high polymer content (compact hairspray) is described for example in international patent application WO 2005/012588 A2.

Although suitable polymers and polymer combinations have been developed for some time now for use in styling concentrates in the field of temporary hair deforming, the previously attained results still have room for improvements, in particular with regard to the storage stability, application, and the holding power of these agents. In particular, currently obtainable styling agents can still be improved insofar as a good combination of holding power and long-term hold (High Humidity Curl Retention) is not always sufficiently ensured.

BRIEF SUMMARY

Cosmetic agents for temporarily deforming keratinic fibers, cosmetic products, and methods for temporarily deforming keratin-containing fibers are provided. In accordance with an exemplary embodiment, a cosmetic agent for temporarily deforming keratinic fibers comprises: a cosmetic preparation comprising: a1) at least one copolymer comprising at least the following monomer units: (meth)acrylic acid; (meth)acrylic acid alkyl ester; and (meth)acrylic acid hydroxy alkyl ester; and a2) at least one copolymer comprising at least the following monomer units: styrene; and acrylic acid and/or methacrylic acid. The proportion by weight of copolymers a1) and a2) in the total weight of the cosmetic preparation is about 10 to about 30% by weight.

In accordance with another exemplary embodiment, a cosmetic product comprises a cosmetic agent comprising a cosmetic preparation comprising: a1) at least one copolymer comprising at least the following monomer units: (meth)acrylic acid; (meth)acrylic acid alkyl ester; and (meth)acrylic acid hydroxy alkyl ester; and a2) at least one copolymer comprising at least the following monomer units: styrene; and acrylic acid and/or methacrylic acid. The proportion by weight of copolymers a1) and a2) in the total weight of the cosmetic preparation is about 10 to about 30% by weight. The cosmetic agent further comprises at least one propellant. The cosmetic product further comprises a dispensing device having a spray valve.

In accordance with a further exemplary embodiment, a method for temporarily deforming keratin-containing fibers comprises providing a cosmetic agent comprising a cosmetic preparation comprising: a1) at least one copolymer comprising at least the following monomer units: (meth)acrylic acid; (meth)acrylic acid alkyl ester; and (meth)acrylic acid hydroxy alkyl ester; and a2) at least one copolymer comprising at least the following monomer units: styrene; and acrylic acid and/or methacrylic acid. The proportion by weight of copolymers a1) and a2) in the total weight of the cosmetic preparation is about 10 to about 30% by weight. The method further comprises applying the cosmetic agent to the keratin-containing fibers.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Cosmetic agents contemplated herein comprise suitable polymer combinations which are characterized by good film-forming and/or firming properties and have a very high holding power, without detriment to the flexibility and good moisture resistance—in particular resistance to perspiration and water. The polymer combination additionally is suitable for the production of concentrated compositions with high chemical and physical stability and is easily applied.

The cosmetic agents contemplated herein comprise a combination of two specific copolymers different from one another.

As contemplated herein, the cosmetic agents provide the following:

1. A cosmetic agent for temporarily deforming keratinic fibers, comprising:
   a) a cosmetic preparation, containing,
   a1) at least one copolymer constructed at least from the following monomer units:
      (meth)acrylic acid
      (meth)acrylic acid alkyl ester
      (meth)acrylic acid hydroxy alkyl ester;
   a2) at least one copolymer constructed at least from the following monomer units:
      styrene
      acrylic acid and/or methacrylic acid,
   wherein the proportion by weight of copolymers a1) and a2) in the total weight of the cosmetic preparation is about 10 to about 30% by weight.
2. The cosmetic agent according to point 1, wherein the proportion by weight of copolymers a1) and a2) in the total weight of the cosmetic preparation is about 11 to about 25% by weight and in particular about 12 to about 20% by weight.
3. The cosmetic agent according to any one of the preceding points, wherein the at least one copolymer a1), in relation to its total weight, consists to an extent of at least about 90% by weight, preferably at least about 95% by weight, and in particular at least about 97% by weight of the monomers
   (meth)acrylic acid
   (meth)acrylic acid alkyl ester
   (meth)acrylic acid hydroxy alkyl ester.
4. The cosmetic agent according to any one of the preceding points, wherein the copolymer a1) bears the INCI name Acrylates/Hydroxyesters Acrylates Copolymer.
5. The cosmetic agent according to any one of the preceding points, wherein the preparation contains, in relation to its total weight, about 1.0 to about 15% by weight, preferably about 2.0 to about 14% by weight, and in particular from about 4.0 to about 12% by weight of copolymer a1).
6. The cosmetic agent according to any one of the preceding points, wherein the at least one copolymer a2), in relation to its total weight, consists to an extent of at least about 90% by weight, preferably at least about 95% by weight, and in particular at least about 97% by weight of the monomers
   styrene
   acrylic acid and/or methacrylic acid.
7. The cosmetic agent according to any one of the preceding points, wherein the at least one copolymer a2), in relation to its total weight, consists to an extent of at least about 90% by weight, preferably at least about 95% by weight, and in particular at least about 97% by weight of the monomers
   styrene
   acrylic acid and/or methacrylic acid
   acrylic acid ester and/or methacrylic acid ester.
8. The cosmetic agent according to any one of the preceding points, wherein the copolymer a2) bears the INCI name Styrene/Acrylates Copolymer.
9. The cosmetic agent according to any one of the preceding points, wherein the preparation contains, in relation to its total weight, about 1.0 to about 15% by weight, preferably about 2.0 to about 14% by weight, and in particular from about 4.0 to about 12% by weight of copolymer a2).
10. The cosmetic agent according to any one of the preceding points, wherein the ratio by weight of copolymer a1) to copolymer a2) is from about 1:7 to about 7:1, preferably from about 1:5 to about 5:1, and in particular from about 1:3 to about 3:1.
11. The cosmetic agent according to any one of the preceding points, wherein the preparation, in relation to its total weight, contains about 30 to about 90% by weight, preferably about 40 to about 85% by weight, and in particular about 50 to about 80% by weight of ethanol.
12. The cosmetic agent according to any one of the preceding points, wherein the preparation, in relation to its total weight, contains about 0.01 to about 30% by weight, and in particular about 5.0 to about 25% by weight of water.
13. The cosmetic agent according to any one of the preceding points, wherein the preparation, in relation to its total weight, consists to an extent of at least about 70% by weight, preferably at least about 80% by weight, and in particular at least about 90% by weight of the copolymers a1) and a2), ethanol, and water.
14. The cosmetic agent according to any one of the preceding points, wherein the preparation a) has a viscosity (Brookfield DV2T viscometer; 20° C., spindle 2, 10 rpm) of from about 10 to about 1000 mPas, preferably from about 15 to about 500 mPas, and in particular from about 20 to about 200 mPas.
15. The cosmetic agent according to any one of the preceding points, wherein the agent also comprises
    b) at least one propellant.
16. The cosmetic agent according to any one of the preceding points, wherein the agent also comprises
    b) at least one propellant from the group of propane, blend of propane and butane, dimethyl ether, and 1,1-difluoroethane.
17. The cosmetic agent according to any one of the preceding points, comprising, in relation to its total weight,
    a) about 30 to about 60% by weight of the cosmetic preparation
    b) about 40 to about 70% by weight of propellant.
18. A cosmetic product, comprising
    i) a cosmetic agent according to any one of points 1 to 17
    ii) a dispensing device having a spray valve.
19. The cosmetic product according to point 18, wherein the spray valve has a maximum valve opening below about 0.4 mm, preferably between about 0.22 and about 0.32 mm, and in particular between about 0.25 and about 0.30 mm.
20. Use of an agent or a product according to any one of points 1 to 19 for temporarily deforming keratin-containing fibers, in particular human hair.
21. A method for temporarily deforming keratin-containing fibers, in particular human hair, in which the keratinic fibers are acted on by a cosmetic agent according to any one of points 1 to 17 and are temporarily fixed in their form.

22. The method according to point 21, wherein the keratinic fibers are acted on with a spray rate of the cosmetic preparation of from about 18 to about 30 g/min, preferably from about 22 to about 28 g/min.

It has been surprisingly found within the scope contemplated herein that, by combining two constituents known per se, which are already used in styling products, an improved moisture resistance of styling products can be obtained. Other properties usually required of styling products, such as lasting hold, stiffness, and low stickiness, are maintained here. A good combination of properties of this type was not anticipated in the knowledge of the individual components and was surprising. It has been found by way of experimentation that a synergistic effect of the two components, i.e. an effect going beyond that of each of the individual components separately, in respect of the moisture resistance and the holding power is obtained by the combination of said two components.

The term 'keratinic fibers', as used herein, includes fur, wool, and feathers, but in particular human hair.

The essential constituents of the cosmetic composition contemplated herein are the anionic copolymer a1) and the anionic copolymer a2), which is different from the copolymer a1).

The cosmetic preparations contemplated herein contain an anionic copolymer a1) as first essential constituent.

With regard to the producibility, application and cosmetic effect of cosmetic agents contemplated herein, it has proven to be advantageous when the proportion by weight of the copolymer a1) in the total weight of the cosmetic preparation a) is about 1.0 to about 15% by weight, preferably about 2.0 to about 14% by weight, and in particular from about 4.0 to about 12% by weight.

The copolymer a1) can be attributed to the monomers (meth)acrylic acid, (meth)acrylic acid alkyl ester, and (meth)acrylic acid hydroxy alkyl ester and optionally further monomers.

Preferred copolymers a1) preferably consist to an extent of at least about 90% by weight, preferably at least about 95% by weight, and in particular at least about 97% by weight of the monomers (meth)acrylic acid, (meth)acrylic acid alkyl ester and (meth)acrylic acid hydroxy alkyl ester. Particularly preferred copolymers a1) were obtained exclusively from the monomers (meth)acrylic acid, (meth)acrylic acid alkyl ester and (meth)acrylic acid hydroxy alkyl ester.

The cosmetic agents of a further preferred embodiment are characterized in that the at least one copolymer a1), in relation to its total weight, consists to an extent of at least about 90% by weight, preferably at least about 95% by weight, and in particular at least about 97% by weight of the monomers (meth)acrylic acid
(meth)acrylic acid alkyl ester
(meth)acrylic acid hydroxy alkyl ester.

The at least one methacrylic acid can be methacrylic acid or acrylic acid.

The alkyl group of the (meth)acrylic acid ester is preferably a C1-C8 alkyl group, which can be linear or branched. Examples of alkyl groups are methyl, ethyl, propyl, isopropyl, 1-butyl, 2-butyl, iso-butyl, tert-butyl, linear or branched pentyl, linear or branched hexyl, linear or branched heptyl, and linear or branched octyl. The alkyl group is more preferably a C1 to C5 alkyl group. In accordance with one embodiment, two or more (meth)acrylic acid alkyl esters are contained, which differ in respect of the carbon number of the alkyl group. By way of example, a methacrylic acid C1-C3 alkyl ester and an acrylic acid C2-C5 alkyl ester are contained.

The hydroxy alkyl group of the (meth)acrylic acid hydroxy alkyl ester can be a hydroxy C1-C10 alkyl group, preferably a hydroxy C2-C5 alkyl group. In a preferred embodiment the (meth)acrylic acid hydroxy alkyl ester unit is a (meth)acrylic acid hydroxy ethyl ester.

The proportion of the (meth)acrylic acid, (meth)acrylic acid alkyl ester and (meth)acrylic acid hydroxy alkyl ester units in the acrylate resin a1) can vary within wide limits. The proportion of the (meth)acrylic acid in the acrylate copolymer is preferably about 2 to about 50% by weight, more preferably about 5 to about 30% by weight. The proportion of the (meth)acrylic acid alkyl ester in the acrylate copolymer is preferably about 5 to about 95% by weight, more preferably about 45 to about 90% by weight. The proportion of the (meth)acrylic acid hydroxy alkyl ester in the acrylate copolymer is preferably about 2 to about 70% by weight, more preferably about 5 to about 30% by weight.

The weight average of the molecular weight of the anionic acrylate copolymer a1) is preferably about 130000 to about 160000, more preferably about 140000 to about 150000, determined by means of gel permeation chromatography (GPC).

The viscosity of the anionic acrylate copolymer a1) used in the cosmetic composition with a solids content of from about 44 to about 46% by weight and a pH of from about 3.30 to about 4.30 at 25° C. is preferably at most about 150 cPS (Brookfield LV, spindle 1, 60 rpm).

The previously described copolymers a1) are sold for example under the name Acudyne® 1000 (INCI name: Acrylates/Hydroxyesters Acrylates Copolymer) by Rohm & Haas.

The cosmetic preparations contemplated herein contain an anionic acrylate copolymer a2) as a second essential constituent.

With regard to the producibility, application and cosmetic effect of cosmetic agents contemplated herein, it has proven to be advantageous when the proportion by weight of the copolymer a2) in the total weight of the cosmetic preparation a) is about 1.0 to about 15% by weight, preferably about 2.0 to about 14% by weight, and in particular from about 4.0 to about 12% by weight.

The copolymer a2) can be attributed to the monomers i) styrene and ii) acrylic acid and/or methacrylic acid and optionally further monomers.

Preferred copolymers a2) preferably consist to an extent of at least about 90% by weight, preferably at least about 95% by weight, and in particular at least about 97% by weight of the monomers styrene and acrylic acid and/or methacrylic acid. Particularly preferred copolymers a2) were obtained exclusively from the monomers styrene and acrylic acid and/or methacrylic acid.

The cosmetic agents of a further preferred embodiment are characterized in that the at least one copolymer a2), in relation to its total weight, consists to an extent of at least about 90% by weight, preferably at least about 95% by weight, and in particular at least about 97% by weight, of the monomers styrene
acrylic acid and/or methacrylic acid
acrylic acid ester and/or methacrylic acid ester.

The previously described copolymers a2) are sold for example under the name Ultrahold® 8 (INCI name Acudyne® Shine (INCI name: Styrene/Acrylates Copolymer; CAS number 9010-92-8) by Dow Chemicals.

The copolymer a2) is used in the cosmetic preparation preferably in partially neutralized or neutralized form. At least one alkanolamine is preferably used for neutralization. The alkanolamines usable as alkalizing agents as contemplated herein are preferably selected from primary amines having a $C_2$-$C_6$ alkyl parent substance carrying at least one hydroxyl group. Particularly preferred alkanolamines are selected from the group formed from 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Alkanolamines that are very particularly preferred as contemplated herein are selected from the group of 2-aminoethan-1-ol, 2-amino-2-methylpropan-1-ol and 2-amino-2-methyl-propan-1,3-diol. A particularly suitable neutralizing agent here has proven to be 2-amino-2-methylpropanol. 2-amino-2-methylpropanol is used in the cosmetic preparations contemplated herein preferably in a quantity that does not exceed the quantity required for neutralization of the copolymer a2). The quantity of 2-amino-2-methylpropanol used in the cosmetic preparations contemplated herein is preferably about 80 to about 100%, particularly preferably about 90 to 100% and in particular about 95 to 100% of the quantity required for full neutralization of the copolymer a2). In a preferred embodiment the proportion by weight of 2-amino-2-methylpropanol in the total weight of the cosmetic preparation is about 0.2 to about 10% by weight, preferably about 0.5 to about 8.0% by weight, and in particular about 1.0 to about 7.0% by weight.

The proportion by weight of the copolymers a1) and a2) in the total weight of the cosmetic preparation is about 10 to about 30% by weight. Cosmetic preparations in which the proportion by weight of the copolymers a1) and a2) in the total weight of the cosmetic preparation is about 11 to about 25% by weight, and in particular about 12 to about 20% by weight, are preferred.

Besides the total proportion by weight of the copolymers a1) and a2), the ratio by weight of the copolymers a1) and a2) to one another also influences the moisture resistance, the holding power, and the further use properties of cosmetic agents contemplated herein. Technically particularly advantageous cosmetic agents are characterized in that the ratio by weight of copolymer a1) to copolymer a2) is from about 1:7 to about 7:1, preferably from about 1:5 to about 5:1, and in particular from about 1:3 to about 3:1.

Besides the previously described copolymers a1) and copolymers a2), the cosmetic preparations can contain further active substances, auxiliaries and nourishing ingredients.

A first group of preferably used active substances are film-forming polymers. These film-forming polymers are not identical to the previously described copolymer a1) or copolymer a2). The proportion by weight of the film-forming polymer in the total weight of the cosmetic preparation is preferably about 0.1 to about 8.0% by weight, preferably about 0.5 to about 6.0% by weight, and in particular about 1.0 to about 4.0% by weight.

Non-ionic polymers are particularly preferably used as film-forming polymers. Suitable non-ionic polymers are, for example:

Vinylpyrrolidone/vinylester copolymers, as are sold for example under the trade name Luviskol® (BASF). Luviskol® VA 64 and Luviskol® VA 73, each vinylpyrrolidone/vinyl acetate copolymers, are preferred non-ionic polymers.

Cellulose ethers, such as hydroxypropyl cellulose, hydroxyethyl cellulose and methyl-hydroxypropyl cellulose, as are sold for example under the trade names Culminal® and Benecel® (AQUALON).

Shellac.

Polyvinylpyrrolidones, as are sold for example under the name Luviskol® (BASF).

Siloxanes. These siloxanes can be either water-soluble or water-insoluble. Both volatile and non-volatile siloxanes are suitable, wherein compounds of which the boiling point at normal pressure is above 200° C. are understood to be non-volatile siloxanes. Preferred siloxanes are polydialkyl siloxanes, such as polydimethyl siloxane, polyalkylaryl siloxanes, such as polyphenylmethyl siloxane, ethoxylated polydialkyl siloxanes, and polydialkyl siloxanes which contain amine groups and/or hydroxyl groups.

Glycosidically-substituted silicones.

Due to their cosmetic effect in combination with the copolymers a1) and a2), film-forming polymers used with preference herein are, in particular, the polyvinylpyrrolidones (INCI name: PVP) and the vinylpyrrolidone/vinyl acetate copolymers (INCI name VP/VA copolymer), wherein the proportion by weight of these polymers is preferably limited to quantities between about 1.0 and about 10% by weight. Particularly preferred cosmetic preparations contemplated herein are therefore characterized in that they also contain, in relation to their total weight, between about 1.0 and about 10% by weight of polyvinylpyrrolidone and/or vinylpyrrolidone/vinyl acetate copolymer, preferably polyvinylpyrrolidone. Particularly preferred cosmetic preparations have a proportion by weight of the polyvinylpyrrolidone and/or vinylpyrrolidone/vinyl acetate copolymer in the total weight of the cosmetic preparation of from about 2.0 to about 8.5% by weight, preferably from about 3.0 to about 7.0% by weight.

To summarize, cosmetic agents that are particularly preferred as contemplated herein with the copolymers a1) and a2) and also the film-forming polymer a3) contain three polymers that are different from one another.

Protein hydrolyzates and/or derivatives thereof can be used as nourishing ingredients. Protein hydrolyzates are product mixtures which are obtained by acid-catalyzed, base-catalyzed or enzyme-catalyzed degradation of proteins. The term 'protein hydrolyzates' is understood in herein to also mean total hydrolyzates and also individual amino acids and derivatives thereof as well as mixtures of different amino acids. The molecular weight of the protein hydrolyzates usable herein lies between about 75, the molecular weight for glycine, and about 200,000, and the molecular weight is preferably about 75 to about 50,000, and very particularly preferably about 75 to about 20,000 daltons.

A further group of nourishing substances are the vitamins, is constituted by the provitamins, vitamin precursors and/or derivatives thereof. Here, vitamins, provitamins and vitamin precursors that are usually assigned to the groups A, B, C, E, F and H are preferred.

Further nourishing substances are glycerol, propylene glycol, panthenol, caffeine, nicotinamide, and sorbitol.

Plant extract, but also monosaccharides or oligosaccharides and/or lipids can also be used as nourishing substance.

The composition of some used cosmetic preparations a) in which the proportion by weight of the copolymers a1) and a2) in the total weight of the cosmetic preparation is about 10 to about 30% by weight, preferably about 11 to about 25% by weight, and in particular about 12 to about 20% by weight, can be deduced form the following tables (values in % by weight relate to the total weight of the cosmetic agent unless specified otherwise).

|  | Formula 1 | Formula 2 | Formula 3 | Formula 4 | Formula 5 |
| --- | --- | --- | --- | --- | --- |
| Copolymer a1) * | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| optional additives | to 100 | to 100 | to 100 | to 100 | to 100 |

|  | Formula 6 | Formula 7 | Formula 8 | Formula 9 | Formula 10 |
| --- | --- | --- | --- | --- | --- |
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| optional additives | to 100 | to 100 | to 100 | to 100 | to 100 |

|  | Formula 11 | Formula 12 | Formula 13 | Formula 14 | Formula 15 |
| --- | --- | --- | --- | --- | --- |
| Copolymer a1) * | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| optional additives | to 100 | to 100 | to 100 | to 100 | to 100 |

|  | Formula 16 | Formula 17 | Formula 18 | Formula 19 | Formula 20 |
| --- | --- | --- | --- | --- | --- |
| Acrylates/Hydroxyesters Acrylates Copolymer (INCI) | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| optional additives | to 100 | to 100 | to 100 | to 100 | to 100 |

Preferred cosmetic agents are based on an aqueous, aqueous/alcoholic or alcoholic carrier. Preferred cosmetic agents thus contain, in relation to their total weight, about 40 to about 98% by weight, preferably about 60 to about 95% by weight, and in particular about 70 to about 92% by weight of polar solvent, preferably polar solvent from the group of water, ethanol and isopropanol.

As already mentioned, the lower alcohols conventionally used for cosmetic purposes having 1 to 4 carbon atoms, such as ethanol and isopropanol, can be contained as alcohols, in particular.

Besides these alcoholic solvents, water-soluble co-solvents can also be used in addition, in particular in combination with water. Examples of particularly preferred co-solvents are glycerol and/or ethylene glycol and/or 1,2 propylene glycol, which are preferably used in a quantity of from 0 to about 30% by weight in relation to the cosmetic preparation a).

Together with the copolymers a1) and a2) described further above, the aqueous, aqueous/alcoholic or alcoholic carriers preferably form an essential constituent of cosmetic preparations a) as contemplated herein. Cosmetic preparations which, in relation to their total weight, consist to an extent of at least about 70% by weight, preferably at least about 80% by weight, and in particular at least about 90% by weight of copolymers a) and a2), ethanol and/or water are particularly preferred.

The composition of some technically advantageous, cosmetic preparations a) with liquid carrier, in which the proportion by weight of the copolymers a1) and a2) in the total weight of the cosmetic preparation is about 10 to about 30% by weight, preferably about 11 to about 25% by weight, and in particular about 12 to about 20% by weight can be deduced from the following tables (the values in % by weight relate to the total weight of the cosmetic agent unless specified otherwise.)

|  | Formula 21 | Formula 22 | Formula 23 | Formula 24 | Formula 25 |
| --- | --- | --- | --- | --- | --- |
| Copolymer a1) * | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| optional additives | to 100 | to 100 | to 100 | to 100 | to 100 |

|  | Formula 26 | Formula 27 | Formula 28 | Formula 29 | Formula 30 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| optional additives | to 100 | to 100 | to 100 | to 100 | to 100 |

|  | Formula 31 | Formula 32 | Formula 33 | Formula 34 | Formula 35 |
|---|---|---|---|---|---|
| Copolymer a1) * | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| optional additives | to 100 | to 100 | to 100 | to 100 | to 100 |

|  | Formula 36 | Formula 37 | Formula 38 | Formula 39 | Formula 40 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| Water and/or ethanol | 40 to 98 | 40 to 98 | 60 to 95 | 60 to 95 | 70 to 92 |
| optional additives | to 100 | to 100 | to 100 | to 100 | to 100 |

*according to claim 1

Of course, not only can the proportion by weight of the liquid carrier in the total weight of the cosmetic preparation a) vary, but the ratio by weight of aqueous to alcoholic carrier is also variable.

Preferred cosmetic preparations contain, in relation to their total weight, about 0.01 to about 30% by weight and in particular about 5.0 to about 25% by weight water.

As already mentioned, the lower alcohols conventionally used for cosmetic purposes having 1 to 4 carbon atoms, such as ethanol and isopropanol, can be contained as alcohols, in particular. Preferred cosmetic preparations contain, in relation to their total weight, about 30 to about 90, preferably about 40 to about 85% by weight, and in particular about 50 to about 80% by weight ethanol.

The composition of some technically advantageous cosmetic preparations a) with liquid carrier, in which the proportion by weight of copolymers a1) and a2) in the total weight of the cosmetic preparation is about 10 to about 30% by weight, preferably about 11 to about 25% by weight, and in particular about 12 to about 20% by weight, can be deduced from the following tables. (The values in % by weight relate to the total weight of the cosmetic agent, unless specified otherwise.)

|  | Formula 41 | Formula 42 | Formula 43 | Formula 44 | Formula 45 |
|---|---|---|---|---|---|
| Copolymer a1) * | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| optional additives | to 100 | to 100 | to 100 | to 100 | to 100 |

|  | Formula 46 | Formula 47 | Formula 48 | Formula 49 | Formula 50 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Copolymer a2) * | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| optional additives | to 100 | to 100 | to 100 | to 100 | to 100 |

-continued

|  | Formula 51 | Formula 52 | Formula 53 | Formula 54 | Formula 55 |
|---|---|---|---|---|---|
| Copolymer a1) * | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| optional additives | to 100 | to 100 | to 100 | to 100 | to 100 |

|  | Formula 56 | Formula 57 | Formula 58 | Formula 59 | Formula 60 |
|---|---|---|---|---|---|
| Acrylates/Hydroxyesters Acrylates Copolymer (INCI) | 1.0 to 15 | 1.5 to 14.5 | 2.0 to 14 | 3.0 to 13 | 4.0 to 12 |
| Styrene/Acrylates Copolymer (INCI) | 1.0 to 15 | 1.5 to 14.5 | 2.0 to 14 | 3.0 to 13 | 4.0 to 12 |
| Ethanol | 30 to 90 | 30 to 90 | 40 to 85 | 40 to 85 | 50 to 80 |
| Water | 0.01 to 30 | 0.1 to 30 | 1.0 to 30 | 2.0 to 30 | 5.0 to 25 |
| optional additives | to 100 | to 100 | to 100 | to 100 | to 100 |

*according to claim 1

The cosmetic preparation is preferably sprayed onto the hair. This is performed particularly preferably with use of a propellant (aerosol spray). Preferred cosmetic agents therefore also comprise at least one propellant b) in addition to the cosmetic preparation a).

Suitable propellants (propellant gases) are propane, propene, n-butane, iso-butane, iso-butene, n-pentane, pentene, iso-pentane, iso-pentene, methane, ethane, dimethyl ether, nitrogen, air, oxygen, nitrous oxide, 1,1,1,3-tetrafluorethane, heptafluoro-n-propane, perfluoroethane, monochlorodifluoromethane, 1,1-difluoroethane, more specifically either individually or in combination. Hydrophilic propellant gases, such as carbon dioxide, can also be used advantageously as contemplated herein if the proportion of hydrophilic gases is selected to be low and lipophilic propellant gas (for example propane/butane) is present in excess. Propane, n-butane, iso-butane and mixtures of these propellant gases are particularly preferred. Preferred cosmetic agents are characterized in that the agent also comprises at least one propellant b) from the group of propane, mixture of propane and butane, dimethyl ether and 1,1-difluoroethane (INCI: Hydrofluorocarbon 152a).

Preferred cosmetic agents contemplated herein contain, in relation to their total weight, about 30 to about 60% by weight of the cosmetic preparation a) and also about 40 to about 70% by weight of propellant b).

The further composition of some preferred cosmetic agents which also comprise a propellant b) in addition to the cosmetic preparation a) and in which the proportion by weight of the copolymers a1) and a2) in the total weight of the cosmetic preparation is about 10 to about 30% by weight, preferably about 11 to about 25% by weight, and in particular about 12 to about 20% by weight, can be deduced from the following table 1.

In table 1, the left-hand column ("Formula x") refers to one of the exemplary cosmetic preparations a) of formulas 1 to 60 specified in the tables presented further above. The other columns two to five ("Propellant") each specify the quantity of propellant combined with the corresponding cosmetic preparation. These values in "% by weight" relate to the total weight of the cosmetic preparation a) of the respective "Formula x" without propellant.

The value "50 to 200% by weight" in the following table 1 corresponds to the addition of propellant to the cosmetic preparation a) in a quantity of from about 50 to about 200% by weight of the weight of the cosmetic preparation a). In other words, the cosmetic preparation a) and the propellant b) are present in this cosmetic agent in a ratio by weight of from about 100:50 to about 100:200 or from about 2:1 to about 1:2.

The cosmetic agents according to row 4, column 4 in the following table 1 are therefore a mixture of the propellant-free cosmetic preparation a) according to formula 3 with a propane/butane mixture in a ratio by weight of cosmetic preparation a) to propellant of from about 100:50 to about 100:200. The entry in row 4, column 4 in other words describes a cosmetic agent for temporarily deforming keratinic fibers, comprising a) a cosmetic preparation, containing,
 a1) about 2.0 to about 14% by weight of at least one copolymer constructed at least from the following monomer units:
  (meth)acrylic acid
  (meth)acrylic acid alkyl ester
  (meth)acrylic acid hydroxy alkyl ester;
 a2) about 2.0 to about 14% by weight of at least one copolymer constructed at least from the following monomer units:
  styrene
  acrylic acid and/or methacrylic acid,
b) propellant from the group propane/butane mixtures,
wherein the proportion by weight of copolymers a1) and a2) in the total weight of the cosmetic preparation is about 10 to about 30% by weight and the ratio by weight of cosmetic preparation a) to propellant b) is about 2:1 to about 1:2.

TABLE 1

| | Propellant [% by weight] | | | |
|---|---|---|---|---|
| Formula 1 | 50 to 200 | 50 to 200 DFE* | 50 to 200 P/B** | 50 to 200 DME*** |
| Formula 2 | 50 to 200 | 50 to 200 DFE* | 50 to 200 P/B** | 50 to 200 DME*** |
| Formula 3 | 50 to 200 | 50 to 200 DFE* | 50 to 200 P/B** | 50 to 200 DME*** |
| Formula 4 | 50 to 200 | 50 to 200 DFE* | 50 to 200 P/B** | 50 to 200 DME*** |
| Formula 5 | 50 to 200 | 50 to 200 DFE* | 50 to 200 P/B** | 50 to 200 DME*** |
| Formula 6 | 50 to 200 | 50 to 200 DFE* | 50 to 200 P/B** | 50 to 200 DME*** |
| Formula 7 | 50 to 200 | 50 to 200 DFE* | 50 to 200 P/B** | 50 to 200 DME*** |
| Formula 8 | 50 to 200 | 50 to 200 DFE* | 50 to 200 P/B** | 50 to 200 DME*** |
| Formula 9 | 50 to 200 | 50 to 200 DFE* | 50 to 200 P/B** | 50 to 200 DME*** |
| Formula 10 | 50 to 200 | 50 to 200 DFE* | 50 to 200 P/B** | 50 to 200 DME*** |
| Formula 11 | 50 to 200 | 50 to 200 DFE* | 50 to 200 P/B** | 50 to 200 DME*** |
| Formula 12 | 50 to 200 | 50 to 200 DFE* | 50 to 200 P/B** | 50 to 200 DME*** |
| Formula 13 | 50 to 200 | 50 to 200 DFE* | 50 to 200 P/B** | 50 to 200 DME*** |
| Formula 14 | 50 to 200 | 50 to 200 DFE* | 50 to 200 P/B** | 50 to 200 DME*** |
| Formula 15 | 50 to 200 | 50 to 200 DFE* | 50 to 200 P/B** | 50 to 200 DME*** |
| Formula 16 | 50 to 200 | 50 to 200 DFE* | 50 to 200 P/B** | 50 to 200 DME*** |
| Formula 17 | 50 to 200 | 50 to 200 DFE* | 50 to 200 P/B** | 50 to 200 DME*** |
| Formula 18 | 50 to 200 | 50 to 200 DFE* | 50 to 200 P/B** | 50 to 200 DME*** |
| Formula 19 | 50 to 200 | 50 to 200 DFE* | 50 to 200 P/B** | 50 to 200 DME*** |
| Formula 20 | 50 to 200 | 50 to 200 DFE* | 50 to 200 P/B** | 50 to 200 DME*** |
| Formula 21 | 50 to 200 | 50 to 200 DFE* | 50 to 200 P/B** | 50 to 200 DME*** |
| Formula 22 | 50 to 200 | 50 to 200 DFE* | 50 to 200 P/B** | 50 to 200 DME*** |
| Formula 23 | 50 to 200 | 50 to 200 DFE* | 50 to 200 P/B** | 50 to 200 DME*** |
| Formula 24 | 50 to 200 | 50 to 200 DFE* | 50 to 200 P/B** | 50 to 200 DME*** |
| Formula 25 | 50 to 200 | 50 to 200 DFE* | 50 to 200 P/B** | 50 to 200 DME*** |
| Formula 26 | 50 to 200 | 50 to 200 DFE* | 50 to 200 P/B** | 50 to 200 DME*** |
| Formula 27 | 50 to 200 | 50 to 200 DFE* | 50 to 200 P/B** | 50 to 200 DME*** |
| Formula 28 | 50 to 200 | 50 to 200 DFE* | 50 to 200 P/B** | 50 to 200 DME*** |
| Formula 29 | 50 to 200 | 50 to 200 DFE* | 50 to 200 P/B** | 50 to 200 DME*** |
| Formula 30 | 50 to 200 | 50 to 200 DFE* | 50 to 200 P/B** | 50 to 200 DME*** |
| Formula 31 | 50 to 200 | 50 to 200 DFE* | 50 to 200 P/B** | 50 to 200 DME*** |
| Formula 32 | 50 to 200 | 50 to 200 DFE* | 50 to 200 P/B** | 50 to 200 DME*** |
| Formula 33 | 50 to 200 | 50 to 200 DFE* | 50 to 200 P/B** | 50 to 200 DME*** |
| Formula 34 | 50 to 200 | 50 to 200 DFE* | 50 to 200 P/B** | 50 to 200 DME*** |
| Formula 35 | 50 to 200 | 50 to 200 DFE* | 50 to 200 P/B** | 50 to 200 DME*** |
| Formula 36 | 50 to 200 | 50 to 200 DFE* | 50 to 200 P/B** | 50 to 200 DME*** |
| Formula 37 | 50 to 200 | 50 to 200 DFE* | 50 to 200 P/B** | 50 to 200 DME*** |
| Formula 38 | 50 to 200 | 50 to 200 DFE* | 50 to 200 P/B** | 50 to 200 DME*** |
| Formula 39 | 50 to 200 | 50 to 200 DFE* | 50 to 200 P/B** | 50 to 200 DME*** |
| Formula 40 | 50 to 200 | 50 to 200 DFE* | 50 to 200 P/B** | 50 to 200 DME*** |
| Formula 41 | 50 to 200 | 50 to 200 DFE* | 50 to 200 P/B** | 50 to 200 DME*** |
| Formula 42 | 50 to 200 | 50 to 200 DFE* | 50 to 200 P/B** | 50 to 200 DME*** |
| Formula 43 | 50 to 200 | 50 to 200 DFE* | 50 to 200 P/B** | 50 to 200 DME*** |
| Formula 44 | 50 to 200 | 50 to 200 DFE* | 50 to 200 P/B** | 50 to 200 DME*** |
| Formula 45 | 50 to 200 | 50 to 200 DFE* | 50 to 200 P/B** | 50 to 200 DME*** |
| Formula 46 | 50 to 200 | 50 to 200 DFE* | 50 to 200 P/B** | 50 to 200 DME*** |
| Formula 47 | 50 to 200 | 50 to 200 DFE* | 50 to 200 P/B** | 50 to 200 DME*** |
| Formula 48 | 50 to 200 | 50 to 200 DFE* | 50 to 200 P/B** | 50 to 200 DME*** |
| Formula 49 | 50 to 200 | 50 to 200 DFE* | 50 to 200 P/B** | 50 to 200 DME*** |
| Formula 50 | 50 to 200 | 50 to 200 DFE* | 50 to 200 P/B** | 50 to 200 DME*** |
| Formula 51 | 50 to 200 | 50 to 200 DFE* | 50 to 200 P/B** | 50 to 200 DME*** |
| Formula 52 | 50 to 200 | 50 to 200 DFE* | 50 to 200 P/B** | 50 to 200 DME*** |
| Formula 53 | 50 to 200 | 50 to 200 DFE* | 50 to 200 P/B** | 50 to 200 DME*** |
| Formula 54 | 50 to 200 | 50 to 200 DFE* | 50 to 200 P/B** | 50 to 200 DME*** |
| Formula 55 | 50 to 200 | 50 to 200 DFE* | 50 to 200 P/B** | 50 to 200 DME*** |
| Formula 56 | 50 to 200 | 50 to 200 DFE* | 50 to 200 P/B** | 50 to 200 DME*** |
| Formula 57 | 50 to 200 | 50 to 200 DFE* | 50 to 200 P/B** | 50 to 200 DME*** |
| Formula 58 | 50 to 200 | 50 to 200 DFE* | 50 to 200 P/B** | 50 to 200 DME*** |
| Formula 59 | 50 to 200 | 50 to 200 DFE* | 50 to 200 P/B** | 50 to 200 DME*** |
| Formula 60 | 50 to 200 | 50 to 200 DFE* | 50 to 200 P/B** | 50 to 200 DME*** |

*"DFE" corresponds to 1,1-difluoroethane
**"P/B" corresponds to a propane/butane mixture
***"DME" corresponds to dimethyl ether Vessels made of metal (aluminum, tinplate, tin), protected plastic or non-splintering plastic, or glass coated externally with plastic are potential compressed-gas containers for aerosol applications, wherein the compressive strength, breaking strength, corrosion resistance, ease of filling and also aesthetic considerations, ease of handling, printability, etc. play a role when selecting such a vessel. Special internal protective coatings ensure resistance to corrosion in respect of the cosmetic agent a).

If the agents contemplated herein are sprayed onto the hair, these agents are advantageously provided with a dispensing device and a spray valve. The resulting cosmetic products accordingly comprise a cosmetic agent as contemplated herein and also a dispensing device having a spray valve. Spray valves which have a maximum valve opening less than about 0.4 mm, preferably between about 0.22 and about 0.32 mm, and in particular between about 0.25 and about 0.30 mm are preferred. The valve opening area is preferably about $60 \times 10^{-3}$ to about $100 \times 10^{-3}$ mm$^2$.

The spray rate in methods contemplated herein is preferably from about 18 to about 30 g/min, in particular from about 22 to about 28 g/min.

Besides being determined by the pressure within the compressed-gas container and the valve opening, the spray rate is also additionally determined by the viscosity of the cosmetic preparation a). Preferred cosmetic agents are characterized in that the preparation a) has a viscosity (Brookfield DV2T viscometer; 20° C., spindle 2, 10 rpm) of from about 10 to about 1000 mPas, preferably from about 15 to about 500 mPas, and in particular from about 20 to about 200 mPas.

In a preferred embodiment the valve has a valve cone coated with a paint or a polymer plastic A and a flexible element with recovery characteristics, which returns the valve after actuation into the closed position (=rest position of the valve). Corresponding cosmetic products in which the aerosol dispensing device comprises a valve which has a valve cone and/or a flexible element with recovery characteristics which is/are coated by a paint or a polymer plastic A are preferred.

In a further preferred embodiment contemplated herein the valve has a flexible element with recovery characteristics and/or a valve cone formed from at least one plastic B, preferably an elastomer plastic. Here too, cosmetic products contemplated herein in which the valve has a flexible element with recovery characteristics and/or a valve cone formed from at least one plastic B are preferred, wherein preferred plastics B are elastomer plastics. Particularly preferred elastomer plastics are selected from Buna, in particular Buna N, Buna 421, Buna 1602 and Buna KA 6712, neoprene, butyl and chlorobutyl.

In a further preferred embodiment contemplated herein the flexible element with recovery characteristics can be formed as a coil spring or coil compression spring. In a further preferred embodiment the flexible element with recovery characteristics can be formed in one piece with the valve cone and can have flexible limbs.

As mentioned in the introduction, the previously described cosmetic agents are characterized by particular hair-related cosmetic properties, in particular advantageous properties in respect of temporary hair deformation. Another embodiment contemplated herein is therefore the use of an agent as contemplated herein for temporarily deforming keratin-containing fibers, in particular human hair.

A further embodiment contemplated herein is a method for temporarily deforming keratin-containing fibers, in particular human hair, in which the keratinic fibers are acted on by a cosmetic agent as contemplated herein and are temporarily fixed in their form.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A cosmetic agent for temporarily deforming keratinic fibers, comprising:
    a) a cosmetic preparation comprising:
        a1) at least one copolymer comprising at least the following monomer units:
            (meth)acrylic acid;
            (meth)acrylic acid alkyl ester; and
            (meth)acrylic acid hydroxy alkyl ester; and
        a2) at least one copolymer comprising at least the following monomer units:
            styrene; and
            acrylic acid and/or methacrylic acid,
        wherein the proportion by weight of copolymers a1) and a2) in the total weight of the cosmetic preparation is about 10 to about 30% by weight; wherein the cosmetic agent exhibits improved stiffness and/or improved moisture resistance of the keratinic fibers as compared to the performance of the cosmetic products that contain only one of copolymer a1) or copolymer a2).

2. The cosmetic agent according to claim 1, wherein the proportion by weight of copolymers a1) and a2) in the total weight of the cosmetic preparation is about 11 to about 25% by weight.

3. The cosmetic agent according to claim 1, wherein the cosmetic preparation, in relation to its total weight, contains about 1.0 to about 15% by weight of copolymer a1).

4. The cosmetic agent according to claim 1, wherein the cosmetic preparation, in relation to its total weight, contains about 1.0 to about 15% by weight of copolymer a2).

5. The cosmetic agent according to claim 1, wherein the cosmetic preparation, in relation to its total weight, contains about 30 to about 90% by weight of ethanol.

6. The cosmetic agent according to claim 1, wherein the cosmetic preparation, in relation to its total weight, contains about 0.01 to about 30% by weight of water.

7. A cosmetic product comprising:
    i) a cosmetic agent comprising:
        a) a cosmetic preparation comprising:
            a1) at least one copolymer comprising at least the following monomer units:
                (meth)acrylic acid;
                (meth)acrylic acid alkyl ester; and
                (meth)acrylic acid hydroxy alkyl ester; and
            a2) at least one copolymer comprising at least the following monomer units:
                styrene; and
                acrylic acid and/or methacrylic acid,
            wherein the proportion by weight of copolymers a1) and a2) in the total weight of the cosmetic preparation is about 10 to about 30% by weight; wherein the cosmetic agent exhibits improved stiffness and/or improved moisture resistance of the keratinic fibers as compared to the performance of the cosmetic products that contain only one of copolymer a1) or copolymer a2); and
        b) at least one propellant; and
    ii) a dispensing device having a spray valve.

8. The cosmetic product according to claim 7, wherein the proportion by weight of copolymers a1) and a2) in the total weight of the cosmetic preparation is about 11 to about 25% by weight.

9. The cosmetic product according to claim 7, wherein the cosmetic preparation, in relation to its total weight, contains about 1.0 to about 15% by weight of copolymer a1).

10. The cosmetic product according to claim 7, wherein the cosmetic preparation, in relation to its total weight, contains about 1.0 to about 15% by weight of copolymer a2).

11. The cosmetic product according to claim 7, wherein the cosmetic preparation, in relation to its total weight, contains about 30 to about 90% by weight of ethanol.

12. The cosmetic product according to claim 7, wherein the cosmetic preparation, in relation to its total weight, contains about 0.01 to about 30% by weight of water.

13. A method for temporarily deforming keratin-containing fibers, the method comprising the steps of:
provising a cosmetic agent comprising:
  a) a cosmetic preparation comprising:
    a1) at least one copolymer comprising at least the following monomer units:
      (meth)acrylic acid;
      (meth)acrylic acid alkyl ester; and
      (meth)acrylic acid hydroxy alkyl ester; and
    a2) at least one copolymer comprising at least the following monomer units:
      styrene; and
      acrylic acid and/or methacrylic acid,
  wherein the proportion by weight of copolymers a1) and a2) in the total weight of the cosmetic preparation is about 10 to about 30% by weight; and
  applying the cosmetic agent to the keratin-containing fibers; wherein the cosmetic agent exhibits improved stiffness and/or improved moisture resistance of the keratinic fibers as compared to the performance of the cosmetic products that contain only one of copolymer a1) or copolymer a2).

14. The method according to claim 13, wherein providing comprises providing the cosmetic agent wherein the proportion by weight of copolymers a1) and a2) in the total weight of the cosmetic preparation is about 11 to about 25% by weight.

15. The method according to claim 13, wherein providing comprises providing the cosmetic agent wherein the cosmetic preparation, in relation to its total weight, contains about 1.0 to about 15% by weight of copolymer a1).

16. The method according to claim 13, wherein providing comprises providing the cosmetic agent wherein the cosmetic preparation, in relation to its total weight, contains about 1.0 to about 15% by weight of copolymer a2).

17. The method according to claim 13, wherein providing comprises providing the cosmetic agent wherein the cosmetic preparation, in relation to its total weight, contains about 30 to about 90% by weight of ethanol.

18. The method according to claim 13, wherein providing comprises providing the cosmetic agent wherein the cosmetic preparation, in relation to its total weight, contains about 0.01 to about 30% by weight of water.

19. The method according to claim 13, wherein providing comprises providing the cosmetic agent that further comprises b) at least one propellant.

* * * * *